United States Patent [19]

Stockton et al.

[11] Patent Number: 4,892,707

[45] Date of Patent: Jan. 9, 1990

[54] APPARATUS FOR THE CALORIMETRY OF CHEMICAL PROCESSES

[75] Inventors: Gerald W. Stockton, Morrisville; Dale H. Chidester, Levittown, both of Pa.; Susan J. Ehrlich, Hamilton Township, Mercer County, N.J.

[73] Assignee: American Cyanamid Company, Stamford, Conn.

[21] Appl. No.: 517,189

[22] Filed: Jul. 25, 1983

[51] Int. Cl.[4] ............................................. G01N 25/20
[52] U.S. Cl. ........................................ 422/51; 374/31; 374/33; 374/34; 422/109; 422/113; 422/117; 422/198; 422/202; 422/225
[58] Field of Search ..................... 165/12, 30, 61–66; 200/208, 215, 255, 256, 426, 445, 446, 469; 374/31, 33, 34; 422/51, 109, 113, 135, 138, 198, 202, 206, 225; 436/147

[56] References Cited

U.S. PATENT DOCUMENTS

| | | | |
|---|---|---|---|
| 2,484,829 | 10/1949 | Holden | 422/109 X |
| 2,733,602 | 2/1956 | Jackson et al. | 374/33 |
| 3,056,664 | 10/1962 | Dravnieks et al. | 422/225 X |
| 3,323,578 | 6/1976 | Hermann | 165/64 X |
| 3,718,437 | 2/1973 | Paloniemi | 422/51 |
| 3,898,051 | 8/1975 | Schmid | 165/61 X |
| 4,208,907 | 6/1980 | Townsend et al. | 422/51 X |
| 4,255,961 | 3/1981 | Biltonen et al. | 374/11 |

OTHER PUBLICATIONS

Bullock; Calorimeter with Automatic Control; J. of Scientific Instruments, vol. 36, 1959, pp. 20–22.
Van Miltenburg; Construction of an Adiabatic Calorimeter: J. chem. Thermodynamics, 1972,4, 773–782.

Primary Examiner—Barry S. Richman
Assistant Examiner—Timothy M. McMahon
Attorney, Agent, or Firm—Estelle J. Tsevdos

[57] ABSTRACT

A calorimeter for measuring the thermodynamic and kinetic characteristics of chemical reactions, microbial fermentations, and other processes of industrial importance is described. The present invention also relates to a method of operation of this apparatus.

17 Claims, 6 Drawing Sheets

APPARATUS FOR THE CALORIMETRY OF CHEMICAL PROCESSES

Chemical reactions are accompanied by the liberation or absorption of energy in the form of heat, and this "heat of reaction" is a definite, reproducible characteristic of a given chemical change. Morever, chemical reactions occur at widely differing rates of speed, and the characteristic time variation of the reaction rate is referred to as "reaction kinetics". The measurement of reaction heat and reaction kinetics is a fundamental part of the experimental development of large-scale chemical manufacturing processes, relating to the optimization and safety of the process and providing design parameters for the manufacturing facility. Any apparatus used for measuring heat is called a calorimeter and numerous prior-art calorimeters have been described covering a wide variety of specific applications. An example of a prior-art calorimeter applied to the study of chemical reactions is described in U.S. Pat. No. 3,994,164.

The invention herein described relates to a new and improved calorimeter designed and optimized for the study of chemical manufacturing processes on a laboratory scale. It is capable of providing accurate measurements of heats of reaction and instantaneous reaction rates. This apparatus offers superior performance and safety of use. The incorporation of a chemically inert, metallic reaction vessel rather than a glass vessel provides a greatly reduced thermal time constant due to the one-thousand fold higher thermal conductivity of the metal. This allows the calorimeter to respond more quickly to thermal fluctuations in the reaction mass, thus lowering the thermal detection threshold and raising the saturating heat flux level. The provision of a thermostatting mechanism for several chemical feed streams external to the reaction vessel provides accurate measurement of the characteristic reaction heat. In the absence of such a mechanism, the reaction mass will be heated or cooled due to the different temperatures of the chemical feed streams. This causes significant measurement errors. The provision of an adiabatic shield makes the present invention impervious to environmental temperature fluctuations, whereas the prior art calorimeter is sensitive to ambient temperature changes. From the point of view of operator safety, the present invention uses a five to ten-fold smaller reaction mass, avoids completely the use of fragile glass vessels, and provides an outstanding pressure relief mechanism of novel design with the largest possible vent orifice for the reaction vessel. These design qualities combine to create a superior calorimeter with a greatly reduced potential explosion hazard, providing a scientific instrument which can be operated with utmost safety in a conventional chemical laboratory. Therefore, the present invention constitutes an advance in the technology of reaction calorimetry and satisfies a need which exists in the art.

In accordance with this invention, a device for use in calorimetric analysis of chemical reactions comprises a cylindrical reaction vessel made of a chemically inert metal and equipped with a gas-tight cover, an agitator mechanism, a temperature sensor, a calibration heater, several inlet pipes, and a two-stage pressure relief mechanism. The reaction vessel is surrounded by an adiabatic shield to eliminate heat flow through the walls and cover of the vessel, thus minimizing thermal noise and errors due to undesired heat conduction paths. Heat can be added to or subtracted from the reaction mass to compensate for the heat of reaction and hold the system isothermal by use of a heat exchanger located under the flat base of the reaction vessel. This heat exchanger comprises a thin insulated metal foil resistive heater attached to a rigid metal plate, the underside of which is cooled by a circulating fluid flowing at a very high rate and maintained at a constant temperature below that of the reaction mass. The electrical power dissipated in the control heater is adjusted to exactly eliminate heat flow from the vessel to the circulating fluid heat sink and to maintain constant the temperature of the reaction mass. When the reaction begins, the power dissipation in the control heater is adjusted to offset the heat flux due to the heat of reaction. Thus, the change in the power dissipation in the control heater is linearly proportional to the rate at which heat is evolved or absorbed by the reaction, where the slope of this proportionality is related to the ratio of the thermal resistances between the heater and the circulating fluid and between the heater and the reaction mass, and the intercept depends upon the temperature differential between the vessel and the circulating fluid. Therefore, the characteristics of the calorimeter can be adjusted during design by selection of values for the above mentioned parameters to maximize sensitivity or, conversely, the saturating heat flux. The thermal characteristics of the calorimeter are further controlled and adjusted by selection of materials of high and low thermal impedance and appropriate dimensions to channel the flow of heat in a desired direction, and, also by the use of thermal barriers such as the aforementioned adiabatic shield.

In the preferred embodiment of the invention, a digital computer is commissioned to acquire the thermal measurements and provide control of the electrical power supplied to the various heat exchanger devices, as well as controlling the delivery of feedstocks and the agitation rate, and performing the calculation and graphical presentation of thermal and kinetic results. In an alternative embodiment of the invention, an analog controller is used in each area where electronic control is required, and the measurements are displayed on an analog recording device.

The design of the preferred embodiment of the invention is optimized for isothermal operation, as heretofore described. However, both adiabatic and temperature scanning modes of operation are also possible. In the isothermal mode, heat is removed from or added to the reaction mass to offset the heat of reaction and maintain the temperature constant. In the adiabatic mode, heat flow to or from the reaction mass is prevented, the heat of reaction remains in the reaction mass, and the temperature of the reaction mass is allowed to rise exponentially as dictated by the thermodynamics and kinetics of the reaction, by tracking the reaction temperature with the adiabatic shield and circulating oil temperatures. In the temperature scanning mode, the temperature of the reaction mass is increased in a stepwise, linear, or other predetermined fashion as required, by raising the temperature of the circulating fluid and adiabatic shield according to a temperature program.

Figure 1:
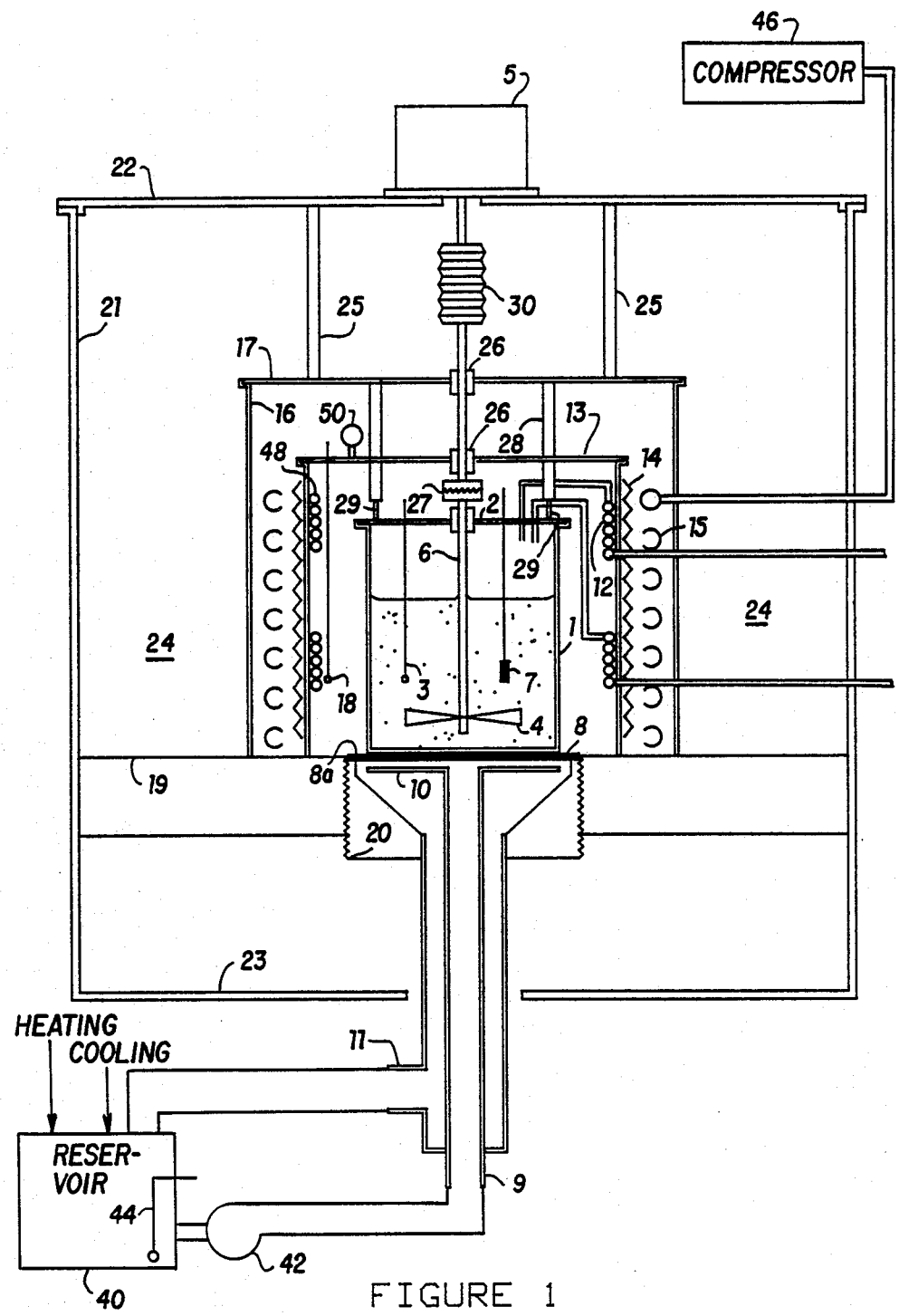
FIG. 1 is a schematic illustration of the mechanical arrangement of the exemplary embodiment of the inventive apparatus, in a cross-sectional view.

The chemical reaction calorimeter was fabricated on a design principle of cylindrical symmetry, as shown in FIG. 1. Viewed from above, the device appears as a set of concentric metal canisters acting as thermal barriers serving different purposes as discussed below. The heart of the calorimeter is a removable reaction vessel, 1, and its cover, 2, which are fabricated from a chemically resistant metal. In the prototype calorimeter, zirconium was used to ensure corrosion resistance to strong mineral acids and bases. The reaction vessel is equipped with a number of devices which are attached to the cover, 2. A high-precision platinum resistance thermometer (RTD), 3, is used to sense the temperature of the reaction mass with a resolution of $5 \times 10^{-4}$°C. The reaction mixture is stirred by an agitator blade, 4, driven by a stepping motor, 5, through a shaft, 6. The vessel contains a resistive heater, 7, used in the calibration of the calorimeter.

The temperature of the reaction mass is carefully regulated by a heat exchanger device made up of heating and cooling elements. This design principle of simultaneous heating and cooling is used in all thermostated regions of the calorimeter to ensure superior temperature control and a short thermal time constant. The vessel's heating is achieved by a circular metal foil resistance heater 8a insulated with 0.001 inch polymer film, and bonded to the topside of a metal disk, 8. The underside of the metal plate, 8, is cooled by a circulating fluid (low viscosity silicone oil in the prototype) flowing from an inlet pipe, 9, flowing radially through the gap between the two circular plates, 8 and 10, and discharging from the outlet pipe 11. The circulating fluid, serving as a heat sink, is supplied from and returned to a reservoir 40 which is simultaneously heated and refrigerated to provide excellent temperature regulation. A pump 42 pumps the fluid to inlet pipe 9. A resistance thermometer 44 senses the temperature of the fluid. The constant temperature difference between the circulating oil and the chemical reaction mass is an important design parameter, as discussed below.

All heat flow to or from the reaction vessel takes place by conduction through its flat base, which is in intimate contact with the heat exchanger mechanism. Heat flow through the walls and cover of the vessel is effectively eliminated by the provision of an adiabatic shield, which maintains the temperature of the space surrounding the reaction vessel equal to the temperature inside the vessel. The adiabatic shield is an air oven contained within a metal canister, 12, and its cover, 13. An insulated foil heater, 14, is bonded to the outer wall of canister, 12, and is cooled by compressed air flowing from numerous ducts, 15 supplied by a compressor 46. The cooling air is contained by a second canister, 16, and cover, 17, and exhausted through a vent pipe (not shown). The temperature of the air space inside the adiabatic shield is sensed by a second platinum resistance thermometer (RTD), 18, and maintained at the temperature of the chemical reaction mass by electronic control.

The heat exchanger mechanism and adiabatic shield canisters are supported by a base block, 19, fabricated from polytetrafluoroethylene, chosen because of its high thermal impedance and suitability for high temperature operation. The body of the heat exchanger, 20, is also made of this material. The entire calorimeter is housed in an outer metal shell, 21, equipped with a cover, 22, and base, 23. The space inside this shell is filled with glass fiber insulation, 24.

Figure 2:
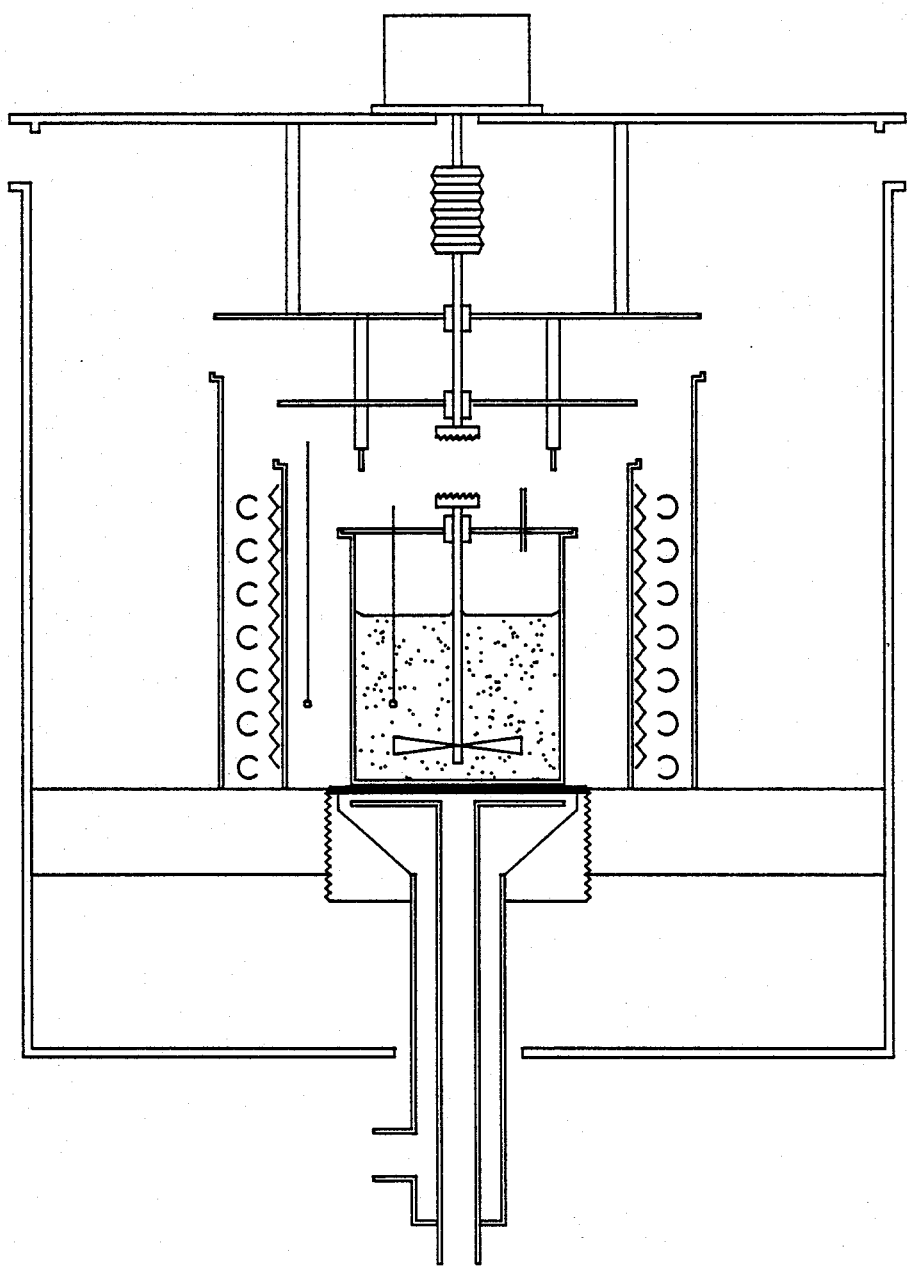
FIG. 2 is an illustration of the facile means of assembly and disassembly of the apparatus through the connection of the various covers and gear coupling of the agitator drive shafts.

The assembly and disassembly of the calorimeter is extremely simple since the inner covers, 13 and 17, are attached to the outer cover, 22, by tubular stand-offs, 25. Thus, all three covers are removed and inserted as a single assembly, as shown in FIG. 2. The agitator shaft, 6, which is supported by integral needle bearings and lip seals, 26, is broken just above the reaction vessel cover, 2, and rejoined by a gear-tooth coupler, 27. The upper gear of the coupler is removed with the outer and inner covers, 13, 17 and 22, and drive motor, 5, and shaft, 6. The lower gear of the coupler is attached to the lower shaft and remains with the reaction vessel, 1, which can be removed separately.

During operation of the calorimeter, fluid chemicals can be added sequentially or simultaneously to the reaction vessel through multiple inlet pipes, 28. The temperature of these "titrants" is pre-equilibrated in a tubular heat exchanger 48 which is in intimate contact with the adiabatic shield canister, 12. This heat exchanger is a stainless steel pipe coiled and bonded to the inside of the canister, and a separate pipe is used for each reactant. The chemicals are mechanically pumped from external reservoirs through the equilibration pipes and into the reaction vessel.

Pressure relief venting of the reaction vessel is achieved on two levels. A small spring loaded relief valve 50 is installed in the cover, 2, and provides a ⅛ inch diameter vent to relieve small overpressures. In the event of a large overpressure exceeding the capacity of the primary vent, the entire cover, 2, of the reaction vessel will move upwards, providing the largest possible vent orifice. The movement of the cover is made possible by the spring loaded cover retainer, 29, and the bellows coupling, 30, for the agitator shaft. The vented vapours exit through pipes in the base of the calorimeter (not shown in FIG. 1).

In the preferred embodiment of the calorimeter, all control and measurement functions are performed using a digital computer to simplify operator interaction and to provide flexibility in the design and application of the control algorithms. In addition, a microprocessorbased controller was incorporated to facilitate timing, switching, and control functions, as well as communication to the host computer.

Figure 3:
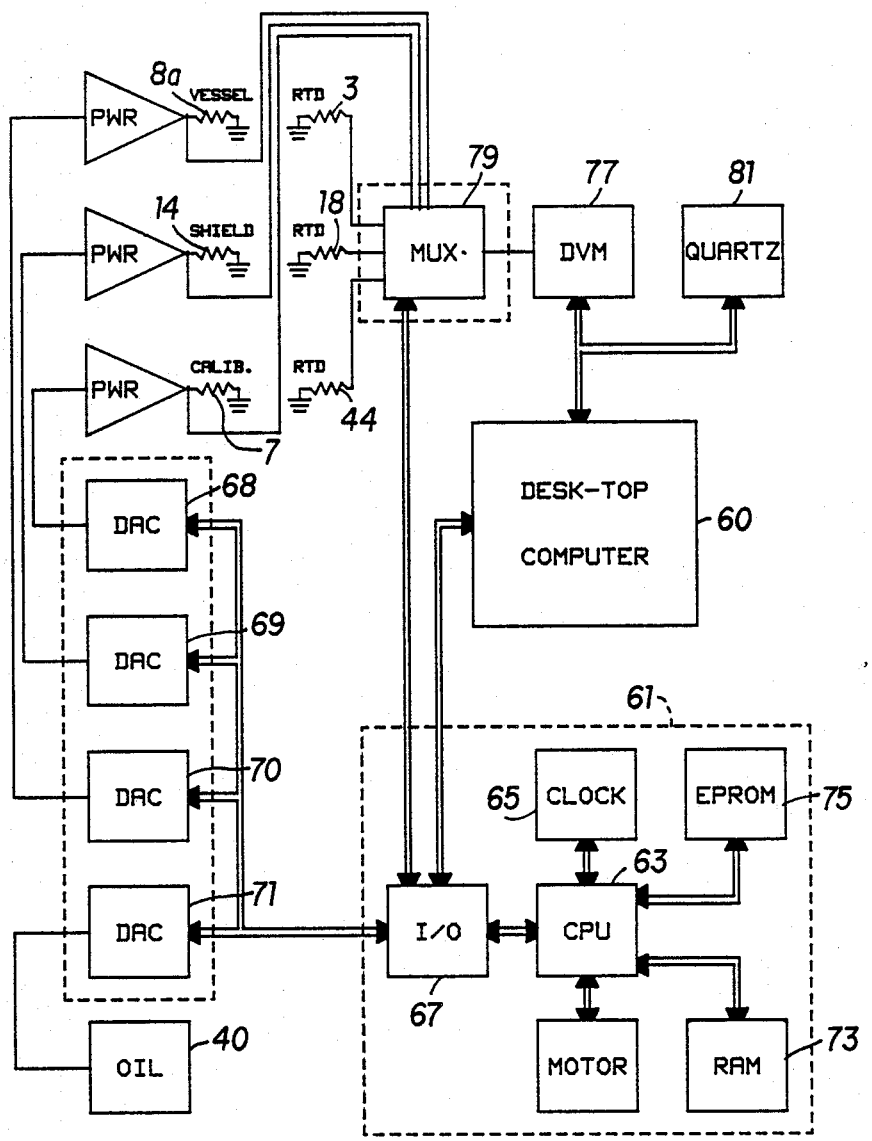
FIG. 3 is a block diagram of the interconnection of the electronic control and measurement components in the preferred embodiment of the invention.

FIG. 3 illustrates the block diagram for the electronic control system. Two different digital interface buses are used: the 16-bit parallel interface allows communication between the computer 60 and the microprocessor 61, while a standard IEEE-488 interface (8-bit parallel/byte serial) was used for communication between the computer and several peripheral devices supplied with this interface protocol.

The microprocessor controller 61 comprises a central processing unit 63, a real time clock/interrupt generator, 65, a digital interface controller 67, a relay multiplexer 68, four high stability digital to analog converters 68-71, random access memory 73, and erasable programmable read only memory 75. The microprocessor provides a convenient means of implementing the interconnection and switching of system components. The acquisition of data, decision making and control functions are performed independently by the digital computer.

A high precision digital 77 is used to make voltage and resistance measurements throughout the system, and is switched between the various input lines by the relay multiplexer 79 under computer control. The resistance measurements of the platinum RTD's 3, 18 and 44 are true 4-wire measurements with D.C. offset compensation for junction effects, providing a resistance thermometer resolution of $5 \times 10^{-4}$°C. The platinum RTD's are calibrated against a 81 reference thermometer (QUARTZ) with an NBS traceable response curve. Power dissipation in the various resistance heaters 7, 8a and 14 is determined by measuring the applied voltage across the heater and multiplying by the current flowing in the circuit. The current is measured independently as the voltage across a precision series current sense resistor divided by its known resistance. Thus, the power measurements are absolute with very high precision.

Electrical power to the heaters is supplied by three programmable power supplies, which are programmed from the computer via three of the four DAC's 68-71. The fourth DAC 71 is used to control and program the oil bath temperature. These 16-bit DAC's provide a control resolution of $2^{16}$ or one part in 65,536.

For the calorimeter described above to provide quantitative thermochemical information, regardless of whether the operating mode is isothermal or temperature scanned, it is necessary for the temperature difference between the chemical reaction mass and the circulating oil heat sink to remain constant. The operation under isothermal conditions is most easily understood. If the temperature set point for the reaction is $T_r$ and that for the oil bath $T_o$, then $T_r > T_o$ and the difference $\Delta T_o = T_r - T_o$ is positive and constant. If the thermal resistance between the heater and the circulating oil is $R_o$ (deg. Watt$^{-1}$), then the power dissipation $q_h$ in the control heater (part 8 in FIG. 1) is given by:

$$q_h = \frac{T_r - T_o}{R_o} \quad (1)$$

Under these steady state conditions, no heat will flow into or out of the reaction vessel and $T_r$ will remain constant. The value of $q_h$ given by Equation (1) represents the baseline for the experiment at a point where no reaction is occurring. When heat is generated in the reaction vessel at a rate $q_r$, due to either chemical reaction or applying electrical power to the calibration heater (part 7 in FIG. 1), this heat must be quickly removed to avoid raising the temperature of the reaction mass. The only available conduction path for heat dissipation is through the bottom of the reaction vessel, through the control heater, into the rapidly circulating oil, and eventual dissipation in the oil reservoir refrigeration system. If the thermal resistance between the reaction mass and the heater is $R_r$, then:

$$T_r - T_o = q_r(R_r + R_o) + q_h R_o \quad (2)$$

Equation (2) rearranges to:

$$\frac{T_r - T_o}{R_o} - q_h = q_r \left(1 + \frac{R_r}{R_o}\right) \quad (3)$$

Since equation (1) indicates that the baseline $q_h$ when $q_r = 0$ is $(T_r - T_o)/R_o$, then the change in $q_h$ when $q_r \neq 0$ is given by the left hand side of Equation (3). Thus, $$\Delta q_h = q_r \left(1 + \frac{R_r}{R_o}\right) \quad (4)$$

Equation (4) suggests that the change in power dissipation in the control heater, $\Delta q_h$, is linearly proportional to the heat generated in the reaction, $q_r$, with a slope determined by the ratio of the thermal resistances $R_r$ and $R_o$ and an intercept of zero. Thus, it is apparent that the heat of a chemical reaction $\Delta H_r$ can be measured by integrating the change in power dissipation in the control heater during the course of the reaction:

$$\Delta H_r = K \int_0^\infty \Delta q_h \cdot dt \quad (5)$$

where the constant $K = R_o/(R_o + R_r)$ is determined during the electrical calibration of the calorimeter.

These observations lead to a number of interesting speculations. The maximum power dissipation in the calorimeter is limited by $R_o$, which should be minimized for a reasonable $\Delta T_o$. The thermal sensitivity of the calorimeter is maximized by making the ratio $R_r/R_o$ large, so that a small reaction heat $q_r$ produces a large change in the control heater power $q_h$. On the other hand, making $R_r/R_o$ small maximizes the heat flux that can be handled by the calorimeter. Since the ratio of the thermal resistances $R_r/R_o$ is adjustable during the fabrication of the calorimeter, and instrument with any desirable characteristic can be constructed.

The dynamic characteristics of the calorimeter can be deduced by constructing a formulation for a resistance/capacitance equivalent circuit which contains an exponential term $[(1 - \exp(-t/T)]$, where T is the system time constant. However, as discussed below, the response of the calorimeter is not limited by this natural time constant due to the use of a control algorithm which gives a greatly reduced effective time constant.

The computer program used to control the calorimeter acquires the temperature measurements from the various sensors, relates the actual temperatures to the desired temperatures (set points), and causes the appropriate response to correct any differences. The mathematical relationship between the error signal $\Delta T$ (= set point - actual temperature) and the corresponding power level in the particular control heater is called the control algorithm. For the adiabatic shield, a conventional PID (proportional/integral/derivative) algorithm is used and found to be satisfactory. The functional form of this algorithm is:

$$q_h = K_1 \cdot \Delta T_s + K_2 \int_0^\infty \Delta T_s \cdot dt + K_3 \cdot \frac{d(\Delta T_s)}{dt} \quad (6)$$

Where $\Delta T_s$ is the error signal for the adiabatic shield.

The coefficients of the three terms in Equation (6), $K_1$, $K_2$, and $K_3$, were optimized experimentally to give a rapid response with minimum overshoot and ringing. The use of the PID algorithm "forces" the calorimeter to respond more quickly than the natural time constant would suggest. The effective time constant can be made a small fraction of the natural constant by adjustment of the coefficients in Equation (6).

The control algorithm for the vessel control heater is novel and was found by experience to give the best control. A PI type of algorithm (no derivative term) with a quadratic dependence on the vessel error signal $\Delta T_c$ was used:

$$q_h = K_4 \cdot \Delta T_c \cdot |\Delta T_c| + K_5 \int_0^\infty \Delta T_c \cdot |\Delta T_c| \, dt \qquad (7)$$

where $|\Delta T_c|$ signifies the absolute value of the error signal.

The effect of this algorithm is to make the heater power $q_h$ essentially constant when $\Delta T_c \neq$ is insignificantly small, but to change $q_h$ more rapidly for larger $T_c$'s than a linear dependence would allow. The consequence of this approach is a noise-free baseline (constant $q_h$) and very rapid return to the set point temperature following a thermal disturbance (e.g., reaction onset). In order to make the thermal responses identical during heating and cooling cycles, different values of the coefficients $K_4$ and $K_5$ were used for positive and negative error signals, $\Delta T_c$. This effectively compensates for the different efficiencies of the heating and cooling elements of the control device.

The operation of the chemical reaction calorimeter is based on a power compensation principle. In order to establish the validity of the heat generation data provided by the calorimeter, it was necessary to determine the linearity of the controller response by calibration and to determine the accuracy of the heat flow measurement by examination of a known chemical system.

Figure 4:
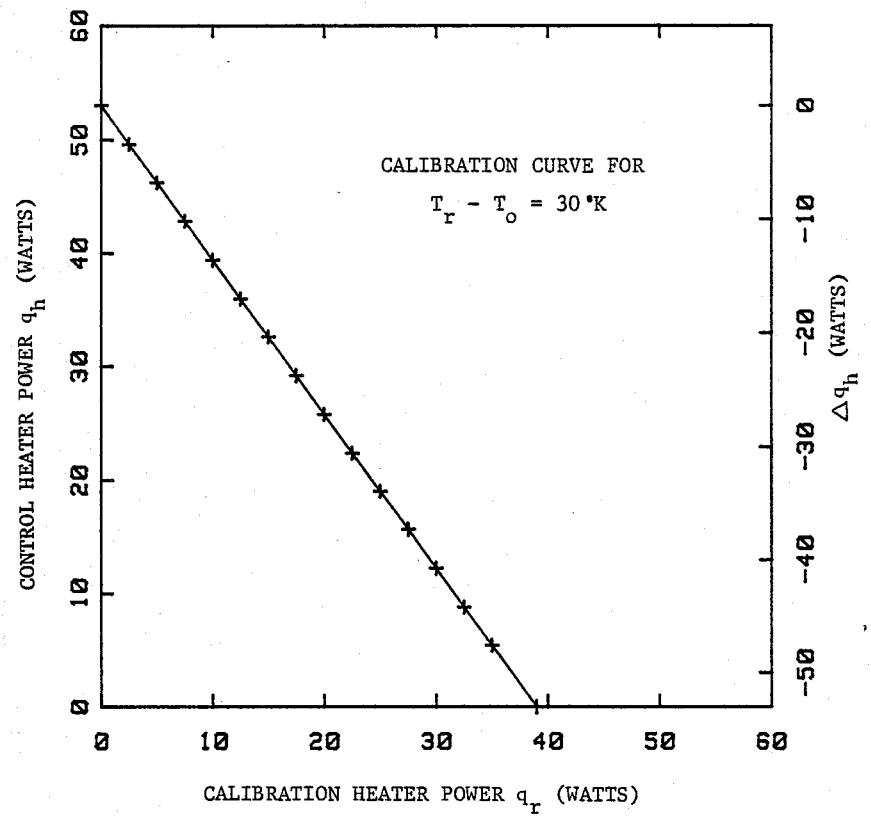
FIG. 4 is a graphical illustration of the linear response of the control heater power as a function of the power dissipated in the calibration heater of the apparatus.

The linearity of the controller power response was determined using a vessel which contained 150 g of water. In this experiment the temperature difference between the reaction vessel and circulating fluid was maintained at 30°K. Electrical power was applied to the calibration heater over a range of 0 to 40 watts. The power response of the control heater was found to be a linear function of calibration heater power, as shown in FIG. 4. The composite thermal resistances, $R_o$ and $R_r$ can be deduced from the slope of this calibration plot and the baseline power $q_h$.

$$R_o = \frac{T_r - T_o}{q_h} \qquad (8)$$

$$R_r = R_o \left[ \frac{\Delta q_h}{q_r} - 1 \right] = R_o \times (\text{slope} - 1) \qquad (9)$$

The value of the calibration constant K (see Equation 5) is:

$$K = \frac{R_o}{R_o + R_r} = \frac{1}{\text{slope}} \qquad (10)$$

Figure 5:
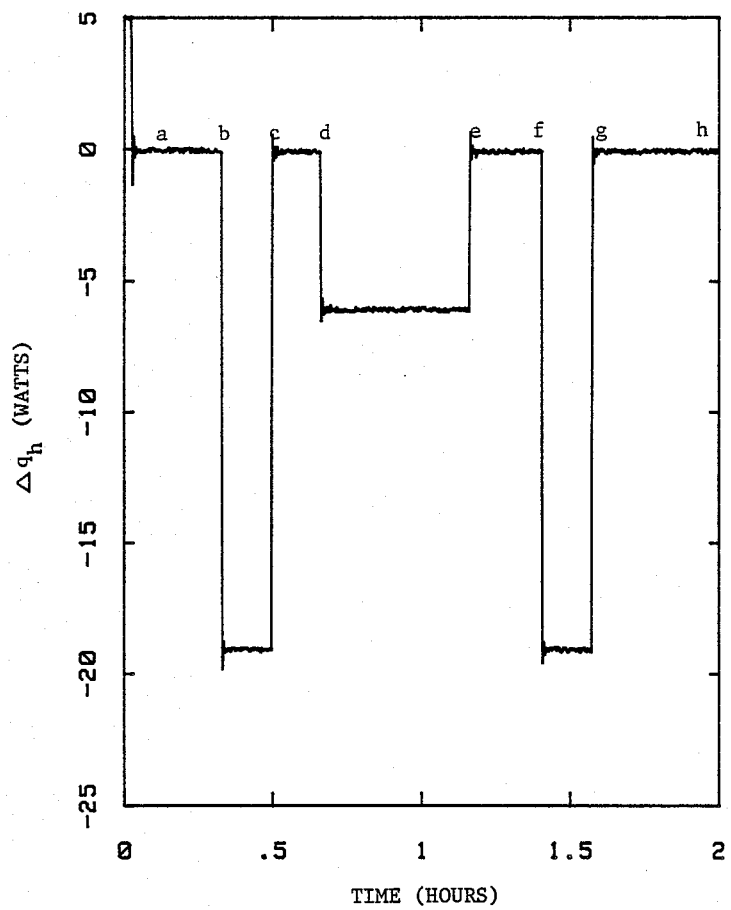
FIG. 5 is a graphical illustration of a typical use of the apparatus in the study of a rapid acid-base reaction.

The performance of the calorimeter was tested by examination of an acid-base neutralization reaction. Four replicate determinations of the enthalpy of neutralization of tris-(hydroxymethyl) aminomethane (TRIS) and hydrochloric acid yielded a mean experimental value of −11.55 kcal/mole, which is in excellent agreement with the reported literature value, −11.55 kcal/mole (1). A typical plot of time vs controller power for this experiment appears in FIG. 5.

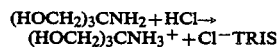

The regions of the plot delineated by a-b, c-d, e-f, and g-h represent the baseline for the experiment. The power excursions in regions b-c and f-g are due to electrical power dissipated in the calibration heater, and the response in region d-e is due to the acid-base neutralization reaction. Because the rate of this proton-exchange reaction is extremely fast relative to the response time of the calorimeter, a boxcar power response curve is obtained with edges corresponding to the start and finish of the titration. Thus, kinetic analysis is not pertinent for this reaction.

Verification of the performance of the calorimeter has been obtained for an organic chemical reaction in a non-aqueous system. The heat of reaction for the ethanolysis of acetic anhydride using p-toluene sulfonic acid (p-TSA) as a catalyst has been determined as −14.38 kcal/mole in four experiments.

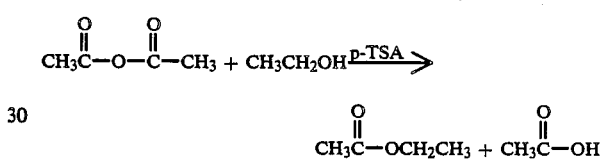

Figure 6:
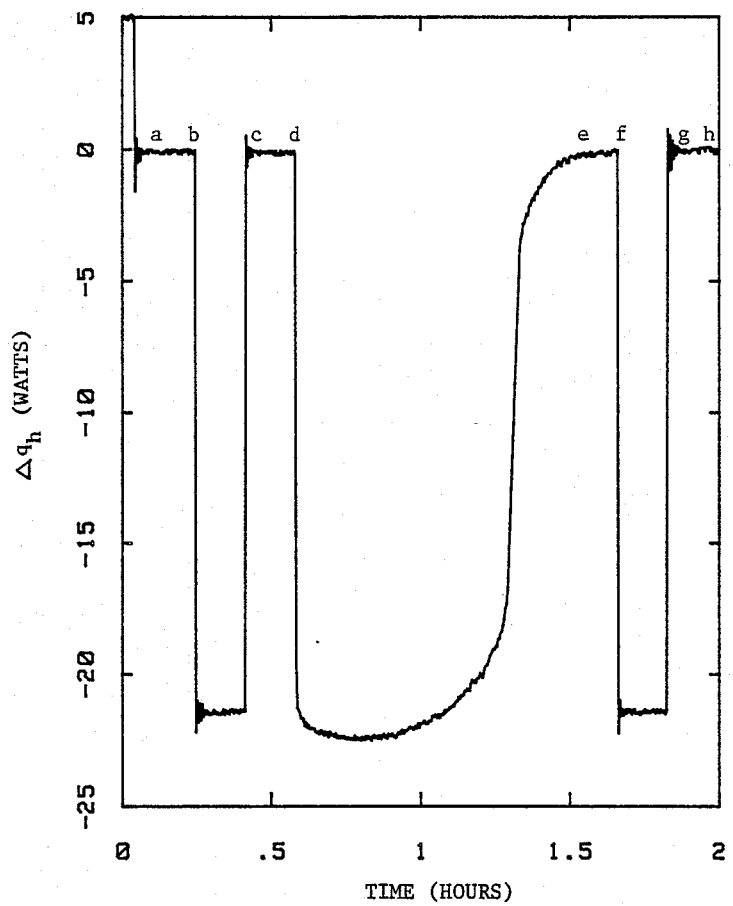
FIG. 6 is a graphical illustration of a slow organic reaction conducted in the apparatus.

An experimentally determined heat of reaction has not been reported in the literature. However, the heat of reaction has been estimated as −14.26 kcal/mole using the computation method of Handrick based on averaged functional group contributions to the heat of combustion of organic compounds (2). The time vs heat flow curve is given in FIG. 6.

As in the previous example, electrical calibration pulses are applied before and after the reaction, which occurs during region d-e. The onset of the power excursion is rapid and a plateau is reached determined by the rate of addition. However, as reagents are consumed, the reaction slows down and the power response decreases. After the reagent addition is complete, the reaction continues for some time with second-order kinetics and the power response decays in concert with this rate law. Analysis of the power curve yields the second-order rate constant for the reaction.

What is claimed is:

1. A calorimeter for use in examining chemical processes in a reaction mass comprising:
   (a) a flat bottomed reaction vessel for containing "a reaction mass;"
   (b) a gas-tight cover for said reaction vessel having at least two chemical inlet ports;
   (c) an agitator mechanism disposed within said reaction vessel;
   (d) a first temperature sensor disposed within said reaction vessel;
   (e) a calibration heater disposed within said reaction vessel;
   (f) a pressure relief mechanism for relieving overpressure in said reaction vessel;
   (g) a heat exchanger in intimate thermal contact with the base of said reaction vessel for regulating heat flow to the vessel and the reaction mass disposed therein;

(h) an adiabatic shield surrounding said reaction vessel, to prevent uncontrolled heat leakage from said vessel, said adiabatic shield comprising a closed barrier vessel having a cover;

(i) means for heating said adiabatic shield;

(j) means for cooling said adiabatic shield;

(k) a second temperature sensor disposed in the space between said adiabatic shield and said reaction vessel;

(l) means for supplying chemical feed streams to said chemical inlet ports;

(m) means to equilibrate the temperature of said chemical feed streams;

(n) means for driving said agitator mechanism located external to said reaction vessel, including a drive shaft passing through said cover of said adiabatic shield and said gas-tight cover of said reaction vessel;

(o) a gear-toothed coupler in said shaft between said reaction vessel cover and adiabatic heat shield cover to permit ease of access to said reaction vessel; and (p) temperature regulation means receiving inputs from said first and second temperature sensors and providing outputs to said calibration heater, said heat exchanger, and said means for heating said adiabatic heat shield.

2. Apparatus according to claim 1, wherein said means to equilibrate comprise a tubular heat exchanger attached to said adiabatic shield and in close thermal contact therewith.

3. Apparatus according to claim 1, wherein said means for heating said adiabatic shield comprise a bonded foil heater and said means for cooling comprise a plurality of ducts for conducting a pressurized gas flow against said adiabatic shield, and means to supply a pressurized gas to said ducts, said control means adapted to maintain the temperature within said adiabatic heat shield equal to the temperature of said reaction mass.

4. Apparatus according to claim 1, wherein said relief mechanism for said reaction vessel comprises a two-stage relief mechanism comprising:

(a) a relief valve located in the cover of said reaction vessel to provide a vent orifice of small diameter to relieve small overpressures; and (b) a collapsible retaining mechanism for the cover of said reaction vessel comprising spring loaded retainers between said cover and said adiabatic heat shield cover and a bellows coupling in said agitator shaft thereby permitting vertical displacement of said reaction vessel cover to provide a large vent orifice to relieve large overpressures.

5. Apparatus according to claim 1, and further including a metal canister having a cover enclosing said adiabatic shield.

6. Apparatus according to claim 5, and further including: a base block supporting said reaction vessel, adiabatic heat shield, and canister, said heat exchanger disposed in said base block; and an outer shell with a cover, surrounding said canister and wherein said cover of said outer shell, said cover of said canister, and said cover of said adiabatic heat shield are connected together along with said means for driving said agitator whereby said covers and said means for driving can be easily removed due to said gear-toothed coupling between said adiabatic shield cover and said reaction vessel cover.

7. Apparatus according to claim 6, wherein said heat exchanger comprises an electric heater attached to a circular metal plate and means for circulating a fluid at a defined temperature for cooling said metal plate; said temperature regulation means regulating said heat exchanger through control of said electric heater.

8. Apparatus according to claim 7, wherein said electric heater comprises a flat circular insulated foil heater bonded to said metal plate and wherein said means for cooling comprise a second plate having an opening in the center thereof closely spaced to said circular plate, an inlet conduit for supplying fluid to said opening in said second plate whereby it will flow from said center toward the edges of said plate; an outlet conduit for collecting fluid from the edges of said plate; a reservoir for said fluid, receiving fluid from said outlet conduit; a pump coupling said reservoir to said inlet conduit; means for heating the fluid in said reservoir; means for cooling the fluid in said reservoir; and a third temperature sensor in said reservoir, said temperature control means responsive to said third temperature sensor to control said means for heating the fluid and means for cooling the fluid to maintain the temperature of said fluid constant.

9. A calorimeter for use in examining chemical processes comprising:

(a) a flat bottomed reaction vessel;

(b) a gas-tight cover for said reaction vessel having at least two chemical inlet ports;

(c) an agitator mechanism disposed within said reaction vessel;

(d) a first temperature sensor disposed within said reaction vessel;

(e) a calibration heater disposed within said reaction vessel;

(f) a pressure relief mechanism for relieving overpressure in said reaction vessel;

(g) a heat exchanger in intimate thermal contact with the base of said reaction vessel for regulating heat flow to the vessel and a reaction mass disposed therein, including means to supply coolant at a determined temperature and flow rate and an electric heater;

(h) an adiabatic shield surrounding said reaction vessel, to prevent uncontrolled heat leakage from said vessel, said adiabatic shield comprising a closed barrier vessel having a cover;

(i) an electrical heater for heating said adiabatic shield;

(j) means for cooling said adiabatic shield with a coolant supplied at constant flow and temperature;

(k) a second temperature sensor disposed in the space between said adiabatic shield and said reaction vessel;

(l) means for supplying chemical feed streams to said chemical inlet ports;

(m) means to equilibrate the temperature of said chemical feed streams;

(n) means for driving said agitator mechanism; and (o) temperature regulation means receiving inputs from said first and second temperature sensors and providing outputs to said calibration heater, said heat exchanger electrical heater, and adiabatic heat shield electric heater and to said means to supply coolant, such as to maintain said defined fluid temperature in said coolant.

10. Apparatus according to claim 9, wherein said means to equilibrate comprises a tubular heat exchanger attached to said adiabatic shield and in close thermal contact therewith.

11. Apparatus according to claim 9, wherein said means for heating said adiabatic shield comprise a bonded foil heater and said means for cooling comprise a plurality of ducts for conducting a pressurized gas flow against said adiabatic shield, said control means adapted to maintain the temperature within said adiabatic temperature equal to the temperature of said reaction mass.

12. Apparatus according to claim 9, wherein said relief mechanism for said reaction vessel comprises a two-stage relief mechanism comprising:
   (a) a relief valve located in the cover of said reaction vessel to provide a vent orifice of small diameter to relieve small overpressures; and
   (b) a collapsible retaining mechanism for the cover of said reaction vessel comprising spring loaded retainers between said cover and said adiabatic heat shield cover and a bellows coupling in said agitator shaft thereby permitting vertical displacement of said reaction vessel cover to provide a large vent orifice to relieve large overpressures.

13. Apparatus according to claim 9, wherein said heat exchanger comprise a circular metal plate, a flat circular insulated foil electric heater bonded to said metal plate, a second plate having an opening in the center thereof closely spaced to said circular plate, and said means for supplying coolant at a defined temperature comprises an inlet conduit coupling said coolant to said opening in said second plate whereby it will flow from said center toward the edges of said plate and an outlet conduit for collecting coolant from the edges of said plate, and further including a reservoir for said fluid, receiving fluid from said outlet conduit; a pump coupling said reservoir to said inlet conduit; means for heating and cooling the fluid in said reservoir; and a third temperature sensor in said reservoir providing an input to said temperature regulation means.

14. Apparatus according to claim 13, wherein said means for driving include a shaft and a gear-toothed coupling between said reaction vessel cover and said adiabatic heat shield cover, and further including a metal canister having a cover enclosing said adiabatic shield, a base block supporting said reaction vessel, adiabatic heat shield, and canister, said heat exchanger disposed in said base block; and an outer shell with a cover, surrounding said canister and wherein said cover of said outer shell, said cover of said canister, and said cover of said adiabatic heat shield are connected together along with said means for driving said agitator whereby said covers and said means for driving can be easily removed due to said gear-toothed coupling between said adiabatic shield cover and said reaction vessel cover.

15. A calorimeter for use in examining chemical processes in a reaction mass comprising:
   (a) a flat bottomed reaction vessel for containing a reaction mass;
   (b) a gas-tight cover for said reaction vessel having at least two chemical inlet ports;
   (c) an agitator mechanism disposed within said reaction vessel;
   (d) a first temperature sensor disposed within said reaction vessel;
   (e) a calibration heater disposed within said reaction vessel;
   (f) a heat exchanger in intimate thermal contact with the base of said reaction vessel for regulating heat flow to the vessel and the reaction mass disposed therein;
   (g) an adiabatic shield surrounding said reaction vessel, to prevent uncontrolled heat leakage from said vessel, said adiabatic shield comprising a closed barrier vessel having a cover;
   (h) means for heating said adiabatic shield;
   (i) means for cooling said adiabatic shield;
   (j) a temperature sensor disposed in the space between said adiabatic shield and said reaction vessel;
   (k) means for supplying chemical feed streams to said chemical inlet ports;
   (l) means to equilibrate the temperature of said chemical feed streams;
   (m) means for driving said agitator mechanism located external to said reaction vessel and having a shaft extending to said agitator;
   (n) a pressure relief mechanism for relieving overpressure in said reaction vessel comprising:
      (i) a relief valve located in the cover of said reaction vessel to provide a vent orifice of small diameter to relieve small overpressures; and
      (ii) a collapsible retaining mechanism for the cover of said reaction vessel comprising spring loaded retainers between said cover and said adiabatic heat shield cover and a bellows coupling in said agitator shaft thereby permitting vertical displacement of said reaction vessel cover to provide a large vent orifice to relieve large overpressures; and
   (o) temperature regulation means receiving inputs from said first and second temperature sensors and providing outputs to said calibration heater, said heat exchanger and said means for heating said adiabatic heat shield.

16. Apparatus according to claim 15, and further including a metal canister having a cover enclosing said adiabatic shield.

17. Apparatus according to claim 15, wherein said means for driving include a shaft and a gear-toothed coupling between said reaction vessel cover and said adiabatic heat shield cover, and further including a metal canister having a cover enclosing said adiabatic shield, a base block supporting said reaction vessel, adiabatic heat shield, and canister, said heat exchanger disposed in said base block; and an outer shell with a cover, surrounding said canister and wherein said cover of said outer shell, said cover of said canister, and said cover of said adiabatic heat shield are connected together along with said means for driving said agitator whereby said covers and said means for driving can be easily removed due to said gear-toothed coupling between said adiabatic shield cover and said reaction vessel cover.

* * * * *